(12) United States Patent
Madabhushi et al.

(10) Patent No.: US 10,937,159 B2
(45) Date of Patent: Mar. 2, 2021

(54) PREDICTING OUTCOME IN INVASIVE BREAST CANCER FROM COLLAGEN FIBER ORIENTATION DISORDER FEATURES IN TUMOR ASSOCIATED STROMA

(71) Applicant: Case Western Reserve University, Cleveland, OH (US)

(72) Inventors: Anant Madabhushi, Shaker Heights, OH (US); Haojia Li, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 16/573,169

(22) Filed: Sep. 17, 2019

(65) Prior Publication Data

US 2020/0242756 A1    Jul. 30, 2020

Related U.S. Application Data

(60) Provisional application No. 62/798,071, filed on Jan. 29, 2019.

(51) Int. Cl.

| | | |
|---|---|---|
| *G06T 7/00* | (2017.01) | |
| *G06K 9/32* | (2006.01) | |
| *G06T 7/11* | (2017.01) | |
| *G06T 7/73* | (2017.01) | |
| *G06T 7/136* | (2017.01) | |
| *G01N 33/574* | (2006.01) | |

(52) U.S. Cl.
CPC .......... *G06T 7/0012* (2013.01); *G06K 9/3233* (2013.01); *G06K 9/3283* (2013.01); *G06T 7/11* (2017.01); *G06T 7/136* (2017.01); *G06T 7/74* (2017.01); *G01N 33/57415* (2013.01); *G01N 2800/52* (2013.01)

(58) Field of Classification Search
None
See application file for complete search history.

(56) References Cited

U.S. PATENT DOCUMENTS

2008/0273787 A1\* 11/2008 Ducksbury ............... G06T 7/90
                                                              382/133
2018/0024064 A1\*  1/2018 Ho ......................... G06T 7/0012
                                                              250/459.1

\* cited by examiner

*Primary Examiner* — Edward Park
(74) *Attorney, Agent, or Firm* — Eschweiler & Potashnik, LLC

(57) ABSTRACT

Embodiments discussed herein relate to accessing a digitized image associated with a patient of tissue demonstrating breast cancer pathology; segmenting a tumor region represented in the digitized image; segmenting collagen fibers represented in the tumor region; computing collagen vectors based on the segmented collagen fibers; generating an orientation co-occurrence matrix based on the collagen vectors; computing a collagen fiber orientation disorder feature based on the co-occurrence matrix; upon determining that the collagen fiber orientation feature exceeds a threshold value: generating a prognosis of the region of tissue as unlikely to experience breast cancer recurrence; upon determining that the collagen fiber orientation feature is less than or equal to the threshold value: generating a prognosis of the region of tissue as likely to experience breast cancer recurrence; classifying the patient as high-risk of recurrence or low-risk of recurrence based, at least in part, on the prognosis; and displaying the classification.

20 Claims, 10 Drawing Sheets

| Feature name | Feature calculation formula |
|---|---|
| orientation difference entropy | $-\sum_{i=0}^{N_g-1} p_{x-y}(i) log(p_{x-y}(i))$ |
| entropy | $-\sum_x \sum_y p(x-y) log(p(x,y))$ |
| orientation difference variance | $-\sum_{i=0}^{N_g-1} i^2 p_{x-y}(i)$ |

Figure 4

PREDICTING OUTCOME IN INVASIVE BREAST CANCER FROM COLLAGEN FIBER ORIENTATION DISORDER FEATURES IN TUMOR ASSOCIATED STROMA

CROSS REFERENCE TO RELATED APPLICATIONS

This application claims the benefit of U.S. Provisional Application 62/798,071 filed Jan. 29, 2019, which is incorporated by reference herein in its entirety.

FEDERAL FUNDING NOTICE

This invention was made with government support under the grant(s) CA199374, CA202752, CA208236, CA216579, and CA220581 awarded by the National Institutes of Health. The government has certain rights in the invention.

BACKGROUND

Breast cancer is the second leading killing cancer for women worldwide. The interaction between tumor and adjacent stromal organization may regulate breast tumor behavior. Collagen fiber organization in the tumor microenvironment plays a crucial role in breast tumor progression and metastasis. Type I collagen fiber orientation in the tumor microenvironment plays an important role in the invasiveness of breast cancer. Personalized treatment for breast cancer requires a precise assessment of cancer aggressiveness or recurrence risk to decide whether it is necessary for the patients to receive adjuvant chemotherapy. Genomic expression based molecular assays have been developed to determine which patients will derive added benefit to chemotherapy, but these existing approaches are expensive and tissue destructive, and require the tissue to be sent to a specified location, for example a lab with high turnover time.

Some existing approaches to quantitative assessment of collagen fiber architecture use advanced imaging techniques including second harmonic generation (SHG) or laser-scanning multiphoton based techniques to correlate the collagen fiber architecture with cancer outcome. However, these techniques are only in research use, and are far from clinical adoption, and are thus not widely available in existing clinical diagnostic or prognostic routines. Currently, there are no validated biomarkers from routine hematoxylin and eosin (H&E) stained images to predict the outcome for breast cancer patients based on collagen fiber organization.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

FIG. 4 illustrates representative collagen orientation disorder features according to various embodiments described herein.

DETAILED DESCRIPTION

Embodiments generate a prognosis of disease free survival for a patient demonstrating ER+ breast cancer, based on collagen fiber orientation disorder features extracted from routine standard of care H&E tissue slides derived from surgically resected specimens. Embodiments may classify a patient demonstrating ER+ breast cancer as high-risk of disease recurrence, or low-risk of disease recurrence based, at least in part, on the prognosis. Embodiments compute a computational histomorphometric biomarker: Collagen Fiber Orientation Disorder from Tumor-associated Stroma (CFOD-TS), based on a collagen vector orientation co-occurrence matrix constructed from H&E stained WSIs. The computational histomorphometric biomarker, CFOD-TS, characterizes the entropy or relative disorderliness of collagen fiber orientation represented in breast cancer WSIs. Embodiments automatically detect collagen fibers represented in an H&E stained WSI and quantitatively determine the relative disorder of the fibers without requiring special stains or advanced microscopy techniques. Embodiments may train a classifier on a homogenous co-operative group clinical trial dataset of hormone positive breast cancer and independently validate the classifier on the TCGA-BRCA (The Cancer Genome Atlas Breast Invasive Carcinoma) dataset. Embodiments thus facilitate an efficient, accurate, and robust prognostic model which may be reproduced beyond a single institution.

Figure 1:
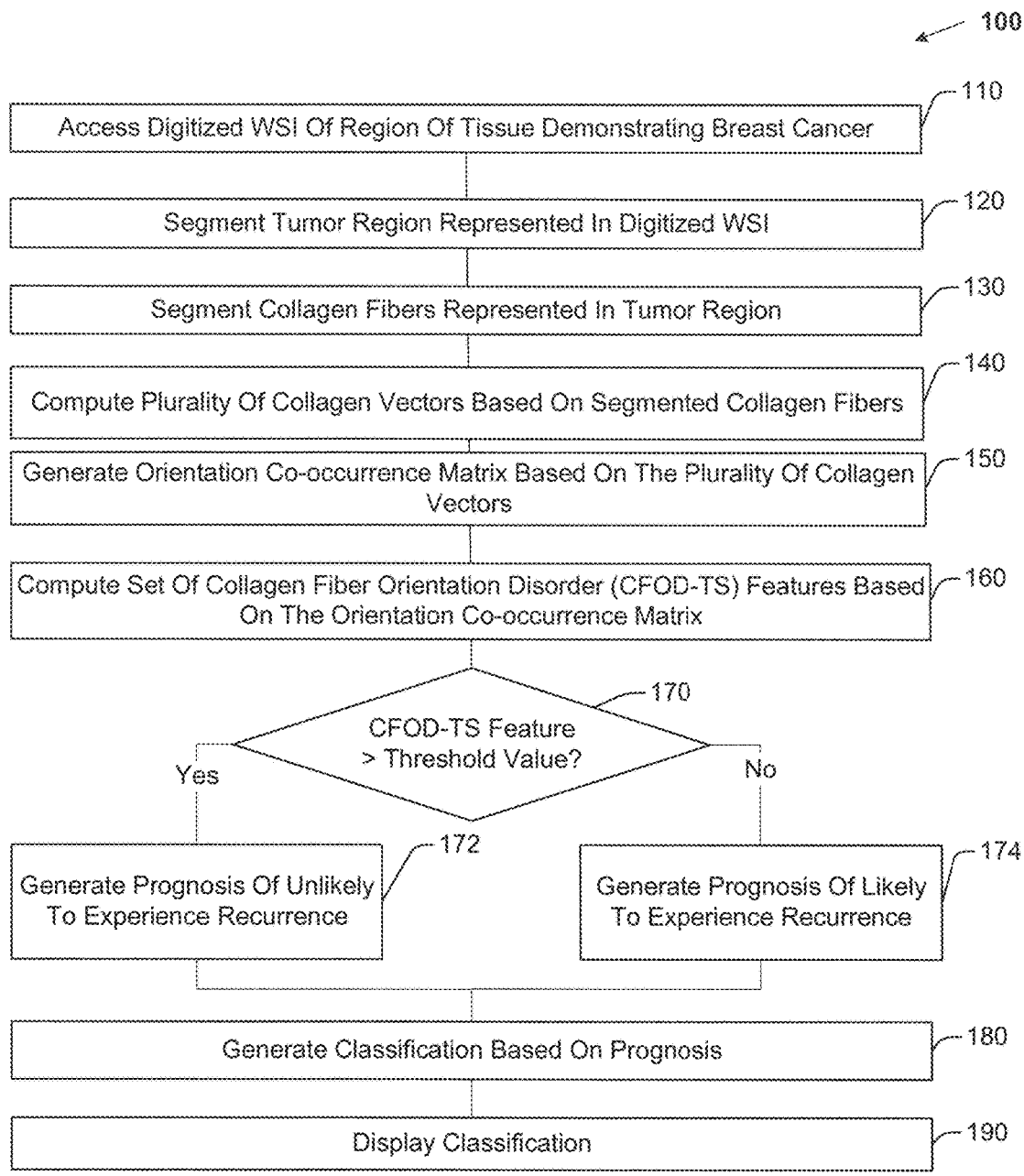
FIG. 1 is a flow diagram of an example methodology or operations for classifying a patient based on a prognosis of disease free survival in breast cancer according to various embodiments described herein.

FIG. 1 is a flow diagram of a methodology or set of operations 100 for generating a prognosis of disease free survival in ER+ breast cancer, and for classifying a patient based on the prognosis. Operations 100 facilitate classifying a patient demonstrating ER+ breast cancer as high-risk of disease recurrence, for example, as likely to experience disease recurrence, or low-risk of disease recurrence, for example, as unlikely to experience disease recurrence, based, at least in part, on the prognosis. Operations 100 may be performed by a processor. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

Operations 100 includes, at 110, accessing a digitized image of a region of tissue demonstrating breast cancer. The digitized image is associated with a patient. In one embodiment, the digitized image is a digitized image of an H&E stained WSI of a region of tissue demonstrating ER+ breast cancer. In another embodiment, other stain types may be employed. In another embodiment, the digitized image may be of a region of tissue demonstrating another, different type of cancer. The region of tissue includes a tumor region. In one embodiment, the tumor region represented in the digitized image has been segmented prior to the implementation of operations 100. In one embodiment, accessing the digitized image may also include accessing clinical data associated with the patient. Accessing the digitized image includes acquiring electronic data, reading from a computer file, receiving a computer file, reading from a computer memory, or other computerized activity not practically performed in a human mind.

Operations 100 also includes, at 120, generating at least one tumor patch. In one embodiment, generating the at least one tumor patch may include automatically segmenting a tumor region represented in the digitized image. For example, deep learning segmentation techniques may be employed to segment a tumor region represented in the digitized image. In another embodiment, other segmentation techniques may be employed. For example, the tumor region may be segmented using Automated Slide Analysis Platform (ASAP), or ImageScope, or other segmentation technique. In one embodiment, the digitized image includes a segmented tumor region, where the tumor region represented in the digitized image has been segmented prior to the implementation of operations 100. In embodiments described herein, the at least one tumor patch may be extracted from within the region defined by the segmented tumor region.

Figure 3:
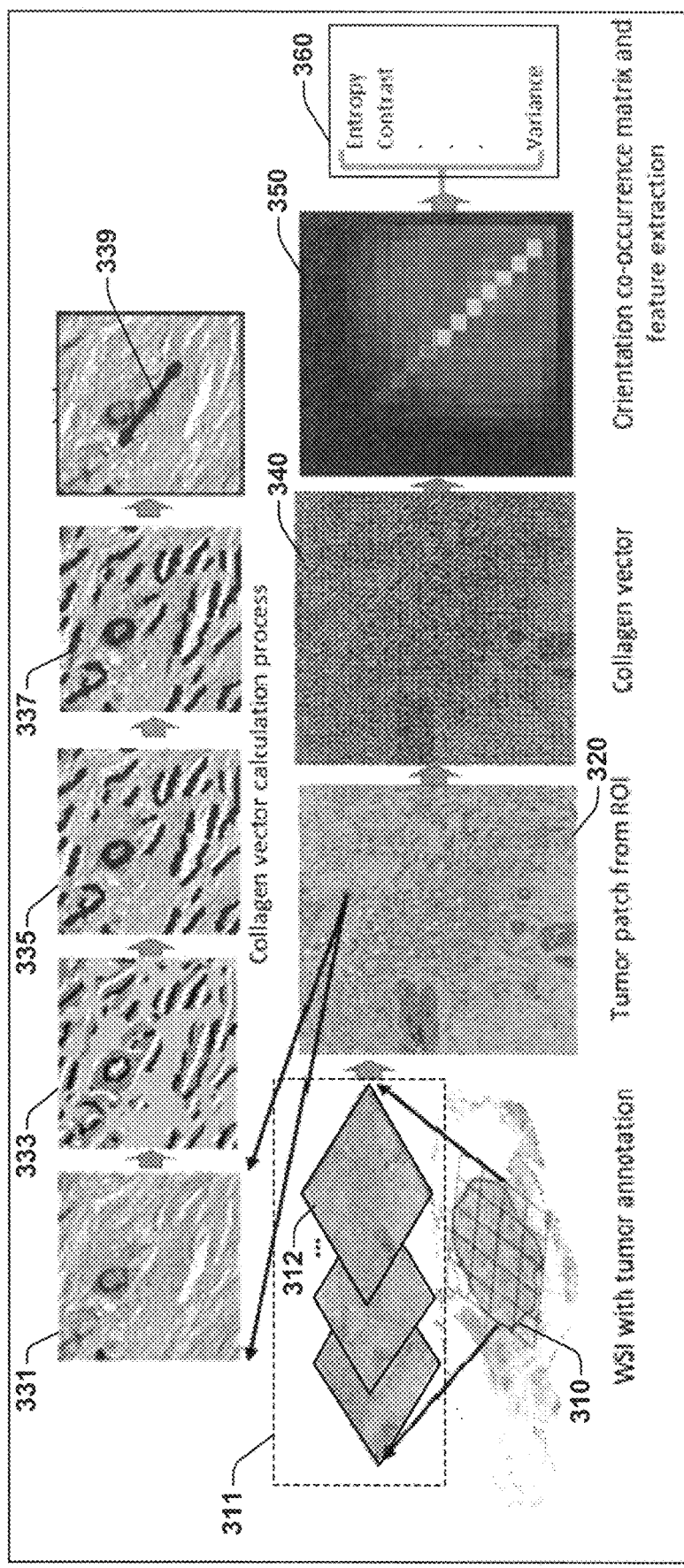
FIG. 3 illustrates a flow diagram of an example methodology or operations for extracting collagen fiber orientation disorder from tumor-associated stroma (CFOD-TS) features according to various embodiments described herein.

FIG. 3 illustrates an exemplary segmented tumor region 310. Generating the at least one tumor patch, in this example, includes extracting a tumor patch from the segmented tumor region 310. FIG. 3 illustrates a plurality of tumor patches 311. The plurality of tumor patches 311 includes tumor patch 312. FIG. 3 also illustrates a magnified representation 320 of the tumor patch 312. In one embodiment, the digitized image is a digitized H&E stained WSI of a region of tissue demonstrating ER+ breast cancer, scanned at 20× magnification. In this embodiment, a tumor patch is a square tumor patch having dimensions of 4000 pixels by 4000 pixels in the x axis and y axis respectively. In another embodiment, other magnification levels, or tumor patch dimensions, may be employed. Generating the at least one tumor patch includes acquiring electronic data, reading from a computer file, receiving a computer file, reading from a computer memory, or other computerized activity not practically performed in a human mind.

Returning to FIG. 1, operations 100 also includes, at 130, segmenting collagen fiber represented in the digitized image. In one embodiment, a Basic Image Feature (BIF) model is employed to segment collagen fiber represented in the digitized image. In this embodiment, each image pixel in the segmented tumor region is assigned a BIF category. In this embodiment, image pixels corresponding to the BIF category sensitive to the tissue linear structure are retrieved, which may be described as a Basic Image Feature of Interest (BIF-OI). An example BIF-OI is illustrated at 335 in FIG. 3. After initially segmenting the collagen fibers, embodiments employ a morphological operation to remove the detected fragments. In one embodiment, a fragment may be defined as a detected linear structure represented in the digitized image, the detected linear structure having fewer than one-hundred (100) pixels. In another embodiment, a fragment may be defined as a detected linear structing having fewer than another, different number of pixels, for example, one-hundred and fifty (150) pixels, or 75 pixels. Since the BIF-OI is not only sensitive to the linear collagen fibers but also to the linear gaps between the cancer cells distributed in a cluster of tumor cells, in order to remove the detected BIF-OI in the epithelial region to enable it to more accurately represent tumor-associated collagen fiber, embodiments may employ a convolutional neural network (CNN) based epithelial detection model to identify the epithelial pixels in the annotated tumor regions, illustrated at 340 in FIG. 3. An epithelial probability mask is generated from the CNN model, where the CNN model is provided the tumor patches as input. The epithelial probability mask has a gray-scale level within the range from 0 to 255. For example, the epithelial probability mask may include a plurality of pixels, where each pixel of the epithelial probability mask has an associated gray-scale level within the range from 0 to 255. The epithelial probability mask is then converted to a binary mask via a threshold. In one embodiment, the threshold value is one-hundred (100). The threshold may be determined by visually inspecting the overlap between the binary epithelial mask and the actual epithelial region represented in tumor patches under different threshold values. Any detected BIF-OIs within the binary epithelial mask are then eliminated. In another embodiment, a threshold percentage or number of the detected BIF-OIs is eliminated, for example, 90%, or 95%. Segmenting collagen fiber represented in the digitized image includes acquiring electronic data, reading from a computer file, receiving a computer file, reading from a computer memory, or other computerized activity not practically performed in a human mind.

Operations 100 also include, at 140, computing a plurality of collagen vectors based on the segmented collagen fibers. In one embodiment, computing the plurality of collagen vectors includes defining the BIF-OI representative of the collagen fiber as $r_i$ with an angle $\Theta(r_i)$ and a length $l(r_i)$ associated with it, illustrated at 337 in FIG. 3. The angle $\Theta(r_i)$ is the angle between the horizontal-axis and the major axis of a fitted ellipse on $r_i$ with the same second-moment ranging between 0 degrees to 180 degrees. The $l(r_i)$ is defined as the number of pixels $r_i$ occupies, illustrated at 337 in FIG. 3. The collagen vector is derived from the window neighborhood by summing the detected collagen fibers in the window via the Parallelogram law. The tumor patch size determines the Field of View used to compute the collagen fiber orientation disorder features, where the small window defines a neighborhood from which a collagen vector is derived. In one embodiment, the window (e.g., small window) is a square window having dimensions of 100 pixels in the x axis by 100 pixels in they axis, where the magnification level is 20×. In another embodiment, other window sizes or magnifications levels may be employed.

In this embodiment, the collagen vector is defined as $v_i$, where the collagen vector has an angle $\Theta(V_i)$, and a length $l(V_i)$, associated with it, illustrated at 339 in FIG. 3. Any collagen vector generated from a window having a high epithelium to stroma ratio is further eliminated from analysis. In one embodiment, a high epithelium to stroma ratio is a ratio greater than one (1). A high epithelium to stroma ratio indicates a window where the area of epithelium is greater than the area of stroma. Since the collagen vector is used to describe the orientation of collagen fibers in the stroma, if there are sufficiently few stroma or collagen fibers in the window, for example, in a window having a high epithelium to stroma ratio, the calculation of the collagen vector in that window would have little or no meaning for the computation of CFOD-TS features, and thus embodiments may eliminate such computations, further improving the performance of embodiments. The $\Theta(V_i)$ and $l(V_i)$ for each collagen vector is calculated based on the coordinate $(X(r_i), Y(r_i))$ of $r_i$ in Cartesian coordinate space converted from polar coordinates, where $i \in 1, 2, \ldots n$ and n is the number of detected collagen fibers in that specific window:

$$\Theta(V_i) = \arctan((X(r_1) + X(r_2) + \ldots X(r_n))/(Y(r_1) + Y(r_2) + \ldots Y(r_n)))$$

$$l(V_i) = \sqrt{(X(r_1) + X(r_2) + \ldots X(r_n))^2/(Y(r_1) + Y(r_2) + \ldots Y(r_n))^2}$$

In this embodiment, the $\Theta(V_i)$ is further discretized by a factor w with the discretized $\overline{\Theta}(V_i)$ angle defined as: $\overline{\Theta}(V_i) = \text{ceil}(\Theta(V_i)/w)$. Computing the plurality of collagen vectors includes acquiring electronic data, reading from a computer file, receiving a computer file, reading from a computer memory, or other computerized activity not practically performed in a human mind.

Operations 100 also includes, at 150, generating an orientation co-occurrence matrix based on the plurality of collagen vectors. In one embodiment, generating the orientation co-occurrence matrix based on the plurality of collagen vectors includes calculating the frequency with which a first collagen vector with a first orientation x co-occurs with a second, different collagen vector having a second orientation y weighted by a corresponding vector length. In one embodiment, generating the orientation co-occurrence matrix further includes normalizing the orientation co-occurrence matrix by computing the total summed matrix element values, and dividing the co-occurrence matrix by the total summed matrix element values. For example, in one embodiment, the orientation co-occurrence matrix is constructed from the at least one tumor patch represented in the WSI based on the collagen vectors calculated from each small window within the tumor patch, as illustrated at 350 in FIG. 3. The orientation co-occurrence matrix is generated by calculating the frequency with which a collagen vector with orientation x co-occurs with a collagen vector with orientation y weighted by the corresponding vector length $l(V_i)$. The matrix is further normalized by dividing the entire matrix by the total summed matrix element values. The element in row x and column y of the orientation co-occurrence matrix is calculated as the following:

$$P(x,y) = (l(V_{x1}) + l(V_{x2}) + \ldots l(V_{xn})) * l(V_{y1}) + l(V_{y2}) + l(V_{yn})),$$

where $\Theta(V_{x1}), \Theta(V_{x2}), \ldots \Theta(V_{xn}) = x$, $\Theta(V_{y1}), \Theta(V_{y2}), \ldots \Theta(V_{yn}) = y$. Generating the orientation co-occurrence matrix based on the plurality of collagen vectors includes acquiring electronic data, reading from a computer file, receiving a computer file, reading from a computer memory, or other computerized activity not practically performed in a human mind.

Operations 100 also includes, at 160, computing a set of collagen fiber orientation disorder from tumor-associated stroma (CFOD-TS) features. Embodiments compute the quantitative measurements of collagen fiber orientation disorder, for example, the CFOD-TS features, based on the orientation co-occurrence matrix. In one embodiment, the CFOD-TS features includes an orientation difference entropy feature. In one embodiment, the orientation different entropy feature may have a value of 0 to 2.89. In another embodiment, the CFOD-TS features include one of an orientation difference entropy feature, an entropy feature, or an orientation difference variance feature. FIG. 4 illustrates table 400, which lists three representative CFOD-TS features extracted from the co-occurrence matrix, and associated feature calculation formulae. In this embodiment, $N_g$ is the dimension of the co-occurrence matrix, indicating the number of discretized orientations of the collagen vector, which is eighteen (18) in this embodiment. In another embodiment, the set of CFOD-TS features may include other, different features, or another, different number of features. Computing the set of CFOD-TS features includes acquiring electronic data, reading from a computer file, receiving a computer file, reading from a computer memory, or other computerized activity not practically performed in a human mind.

Operations 100 also includes, upon determining at 170 that a member of the set of collagen fiber orientation features exceeds a threshold value, generating, at 172, a prognosis of the region of tissue as unlikely to experience breast cancer recurrence. Generating the prognosis includes acquiring electronic data, reading from a computer file, receiving a computer file, reading from a computer memory, or other computerized activity not practically performed in a human mind.

Operations 100 may also include, upon determining at 170 that the member of the set of collagen fiber orientation features is less than or equal to the threshold value, generating, at 174, a prognosis of the region of tissue as likely to experience breast cancer recurrence. Generating the prognosis includes acquiring electronic data, reading from a computer file, receiving a computer file, reading from a computer memory, or other computerized activity not practically performed in a human mind.

In one embodiment, determining that a member of the set of collagen fiber orientation features exceeds a threshold value, at 170, or determining at 170 that the member of the set of collagen fiber orientation features is less than or equal to the threshold value, the threshold value is 2.25. In another embodiment, the threshold value may be another, different value. For example, the threshold value may be a median value of the most prognostic feature as determined based on a training set of digitized WSIs according to techniques described herein.

Operations 100 also includes, at 180, generating a classification of the patient. Embodiments may generate a classification of the patient as high-risk of recurrence or low-risk of recurrence based, at least in part, on the prognosis. For example, embodiments may classify a patient as high-risk of recurrence when a prognosis of the region of tissue as likely to experience breast cancer recurrence is generated at 174. Embodiments may classify a patient as low-risk of recurrence when a prognosis of the region of tissue as unlikely to experience breast cancer recurrence is generated at 172. In one embodiment, where the at least one tumor patch includes a plurality of tumor patches, embodiments may compute the median value of the collagen fiber orientation feature(s) extracted from the plurality of tumor patches, and compute the recurrence risk based on the median value of the collagen fiber orientation features extracted from the plurality of tumor patches. Embodiments may classify a patient as a member of a positive class, for example, high-risk of recurrence, based upon the prognosis, or may classify the patient as a member of a negative class, for example, low-risk of recurrence, based upon the prognosis. Embodiments may further base the classification on clinical data associated with the patient.

Operations 100 further includes, at 190, displaying the classification. Operations 100 may also include, at 190, optionally displaying the prognosis, the member of the set of collagen fiber orientation features, a value associated with the member of the set of collagen fiber orientation features, the orientation co-occurrence matrix, a member of the plurality of collagen vectors, or the digitized image. Displaying the classification or optionally displaying the prognosis, the member of the set of collagen fiber orientation features, a value associated with the member of the set of collagen fiber orientation features, the orientation co-occurrence matrix, a member of the plurality of collagen vectors, or the digitized image may include displaying the classification or optionally displaying the prognosis, the member of the set of collagen fiber orientation features, a value associated with the member of the set of collagen fiber orientation features, the orientation co-occurrence matrix, a member of the plurality of collagen vectors, or the digitized image on a computer monitor, a smartphone display, a tablet display, or other displays. Displaying the classification or optionally displaying the prognosis, the member of the set of collagen fiber orientation features, a value associated with the member of the set of collagen fiber orientation features, the orientation co-occurrence matrix, a member of the plurality of collagen vectors, or the digitized image may also include printing the classification or the prognosis, the member of the set of collagen fiber orientation features, the orientation co-occurrence matrix, a member of the plurality of collagen vectors, a value associated with the member of the set of collagen fiber orientation features, or the digitized image. Displaying the classification or optionally displaying the prognosis, the member of the set of collagen fiber orientation features, a value associated with the member of the set of collagen fiber orientation features, the orientation co-occurrence matrix, a member of the plurality of collagen vectors, or the digitized image may also include controlling a breast cancer classification system, a personalized medicine system, a computer assisted diagnostic (CADx) system, a monitor, or other display, to display operating parameters or characteristics of a classifier, including a machine learning classifier, during both training and testing, or during clinical operation of the classifier. By displaying the classification or optionally displaying the prognosis, the member of the set of collagen fiber orientation features, a value associated with the member of the set of collagen fiber orientation features, the orientation co-occurrence matrix, a member of the plurality of collagen vectors, or the digitized image, example embodiments provide a timely and intuitive way for a human pathologist or other medical practitioner to more accurately classify a breast cancer patient or generate a prognosis of disease free survival in breast cancer, thus improving on existing approaches to classifying a breast cancer patient, generating a prognosis for disease free survival in breast cancer, or for determining an adjuvant chemotherapy dosing schedule for a breast cancer patient.

Some portions of the detailed descriptions herein are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 2:
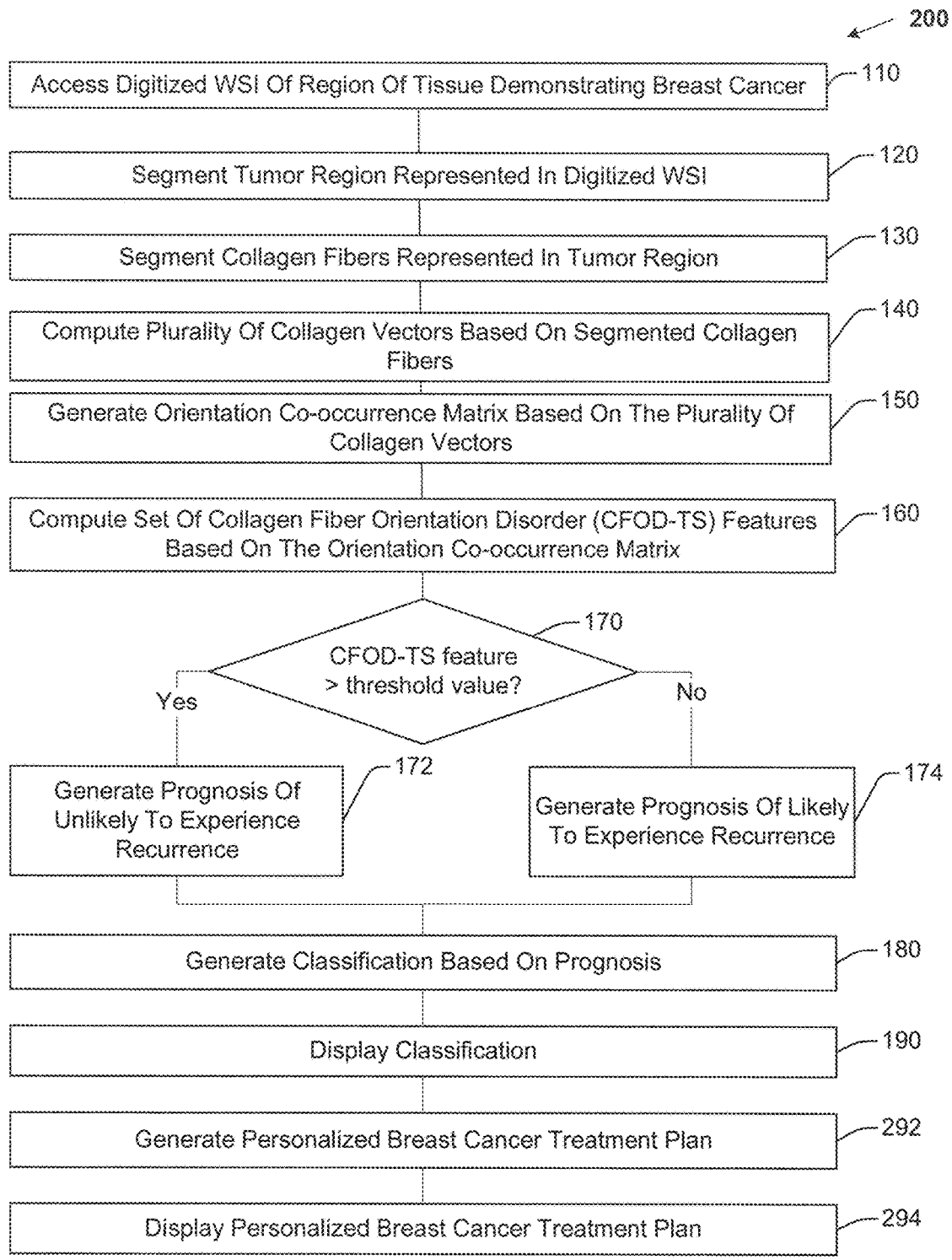
FIG. 2 is a flow diagram of an example methodology or operations for classifying a patient based on a prognosis of disease free survival in breast cancer according to various embodiments described herein.

FIG. 2 is a flow diagram of example operations 200 that is similar to operations 100 but that includes additional details and elements. Operations 200 also includes, at 292, generating a personalized breast cancer treatment plan based, at least in part, on the classification. For example, operations 200 may include, at 292 computing a first dosage or dosage schedule of a first adjuvant chemotherapy agent based, at least in part, on the classification when the patient is classified as a member of the positive class, for example, high-risk of recurrence, or a second dosage or dosage schedule of a second, different adjuvant chemotherapy agent based, at least in part, on the classification when the patient is classified as a member of the negative class, for example, low-risk of recurrence. Different personalized treatment plans may also generate different follow-up or monitoring schedules depending on the classification. For example, a patient classified as high-risk of recurrence may be scheduled, according to the personalized breast cancer treatment plan, more frequent monitoring, than a patient classified as low-risk of recurrence. In this embodiment, operations 200 further include at 294, displaying the personalized breast cancer treatment plan according to various techniques described herein. In one embodiment, the personalized breast cancer treatment plan may be further based on the prognosis, or the digitized image. In one embodiment, the personalized breast cancer treatment plan may be further based on clinical data associated with the patient.

Figure 10:
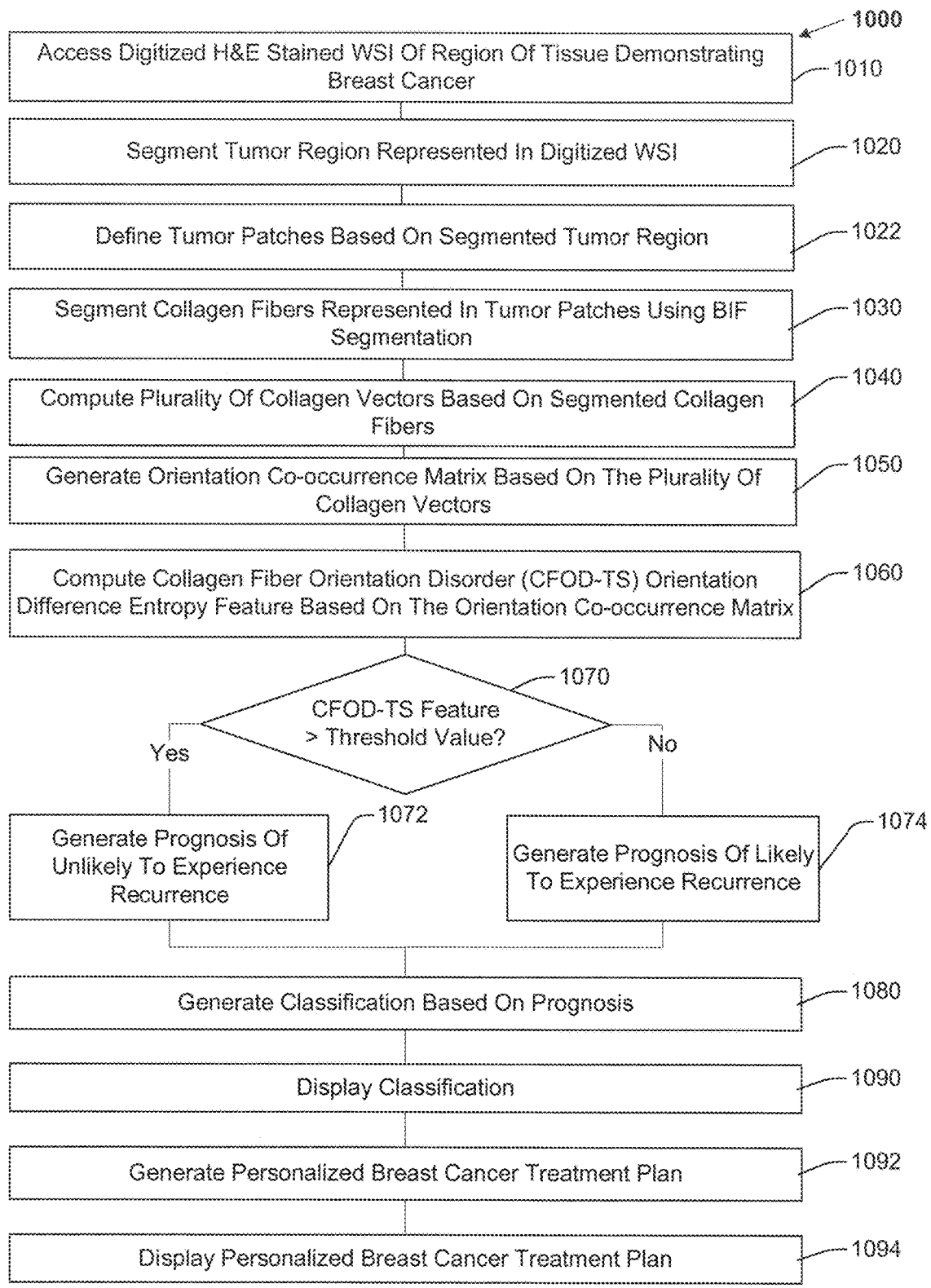
FIG. 10 is a flow diagram of an example methodology or operations for classifying a patient based on a prognosis of disease free survival in breast cancer according to various embodiments described herein.

While FIGS. 1, 2, and 10 illustrate various actions occurring in serial, it is to be appreciated that various actions illustrated in FIG. 1, FIG. 2, or FIG. 10, could occur substantially in parallel. By way of illustration, a first process could involve accessing a digitized H&E stained WSI, a second process could involve detection of collagen fiber represented in the digitized H&E stained WSI, and a third process could involve calculation of a collagen vector based on the detected collagen fiber. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including methods or operations 100 or 200 or 1000, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Techniques and aspects of various embodiments are further explained below, in connection with an example embodiment that facilitates generating a prognosis of disease free survival for an ER+ breast cancer patient represented in medical imagery, including a digitized H&E stained WSI, and of classifying the patient.

Example Use Case: Breast Cancer Prognosis Using Collagen Fiber Orientation Disorder from Tumor-Associated Stroma (CFOD-TS)

An example embodiment included training a classifier to generate a prognosis of disease free survival for an ER+ breast cancer patient based on collagen fiber orientation disorder from tumor-associated stroma (CFOD-TS) features extracted from H&E stained WSIs of tissue demonstrating breast cancer. CFOD-TS is a quantitative measurement of disorder degree of collagen fibers orientation within the tumor-associated stroma. CFOD-TS is computed from the orientation co-occurrence matrix constructed from the collagen vectors, which in turn are calculated based on the detected collagen fibers on H&E stained WSI.

FIG. 3 illustrates one example workflow used to extract CFOD-TS. In one example, invasive breast cancer regions, illustrated by segmented tumor region 310, in WSIs are automatically annotated using a convolutional neural network segmentation technique, or may be annotated by an expert breast pathologist. A plurality of tumor patches 311 is extracted from the annotated breast cancer tumor regions 310, where an enlargement of tumor patch 312 is illustrated at 320. Collagen fibers are segmented, in this example using a Basic Image Feature (BIF) based approach, based on which collagen vectors are derived, illustrated at 331-339. Collagen vectors are calculated at 340. An orientation co-occurrence matrix 350 is then generated from collagen vectors in the tumor patch(es) followed by extraction of the CFOD-TS feature(s) at 360 from the co-occurrence matrix 350.

In one example, a dataset comprising H&E stained WSIs of 234 (71 recurrence) ER+ breast cancer patients with HR-positive or negative breast cancer, 0 to 3 positive lymph nodes from the prospective, randomized, multi-site clinical trial ECOG-ACRIN (Eastern Cooperative Oncology Group-American College of Radiology Imaging Network) E2197 study was acquired as the training set. H&E stained WSIs of 171 (26 recurrence) patients with ER+ breast cancer across various tumor stages from multiple institutions from the publicly available TCGA-BRCA were collected as an independent validation set. The disease free survivals corresponding to all the patients were collected as the experimental outcome.

Figure 5:
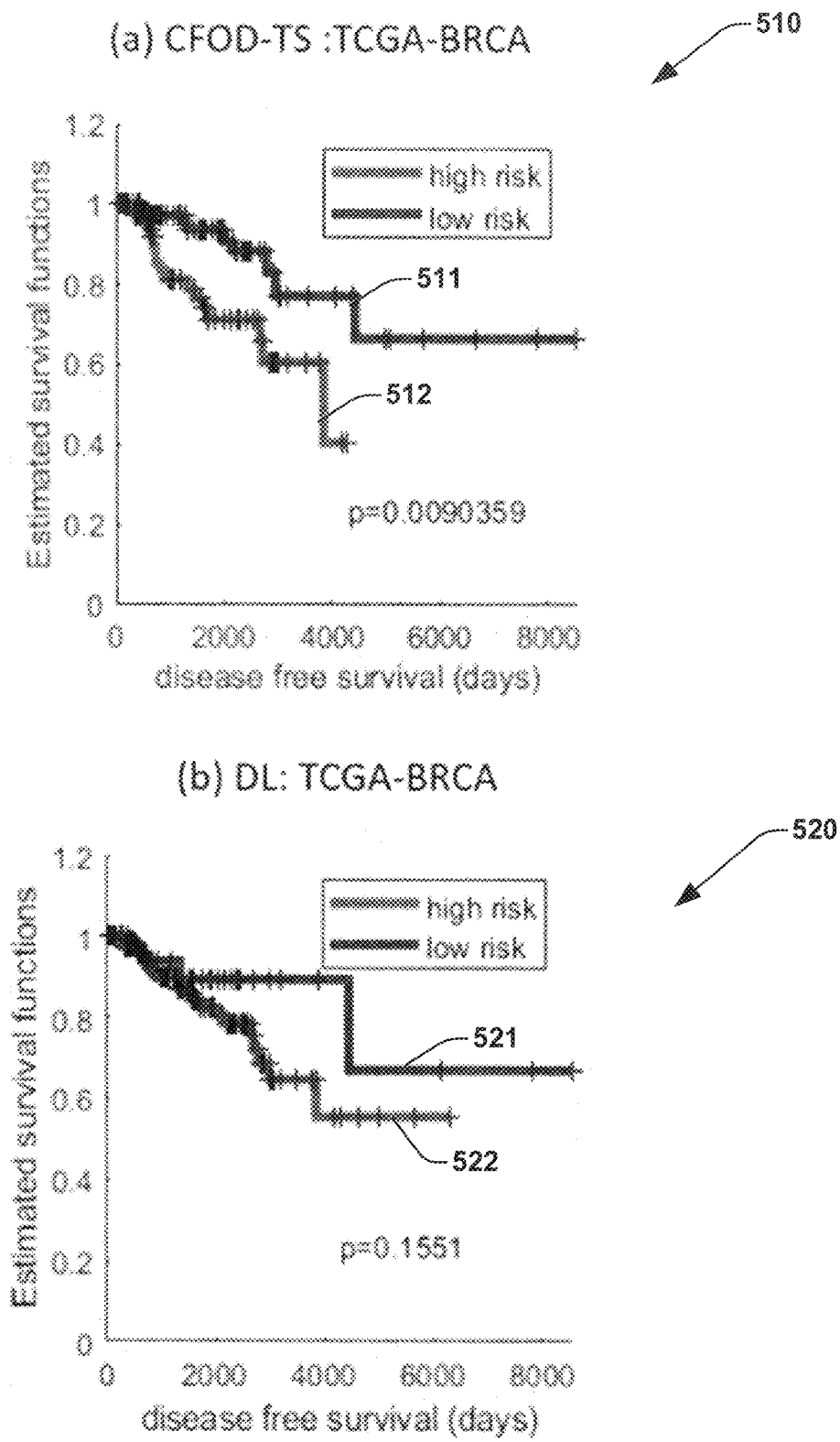
FIG. 5 illustrates Kaplan-Meier estimator curves based on CFOD-TS derived risk groups according to various embodiments described herein, and based on deep learning derived risk groups.

In one example, a set of features describing CFOD-TS were extracted from multiple tumor patches having dimensions of 4000 pixels in the x axis by 4000 pixels in the y axis, at 20× magnification, in WSIs. Other, different patch sizes may be employed, for example 2000 pixels by 2000 pixels. Among all the extracted features, CFOD-TS feature orientation difference entropy was identified as the feature distinguishable or most discriminative between the patients with recurrence and patients without recurrence with a follow-up longer than fifteen (15) years and also significantly correlated with the disease free survival for recurrent patients for ECOG-ACRIN E2197. The CFDO-TS derived risk groups stratified the patients into high-risk-recurrence and low-risk-recurrence groups. The p value from log-rank test for disease free survival between the patients in the high-risk group and the patients in the low-risk group was 0.0057 for ECOG-ACRIN E2197. The Kaplan Meier (KM) estimator curves and the p value from log-rank test for TCGA-BRCA according to embodiments are shown in FIG. 5 at 510, which showed that the disease free survival for the low risk group, illustrated by the low-risk group KM curve 511, is significantly higher than that in the high risk group, illustrated by the high-risk group KM curve 512. Hazard Ratio (HR) between the two risk groups (high-risk, low-risk) was 7.11 (n=104, 95% CI=1.53-32.94, p=0.01) for stage I/II tumors and 3.03 (n=39, 95% CI=0.79-8.67, p=0.11) for stage III/IV cancers for TCGA-BRCA. The Kaplan Meier (KM) estimator curves and the p value from log-rank test for TCGA-BRCA according to a deep learning model, according to existing approaches, are illustrated at 520, with the high-risk group KM curve illustrated at 522 and the low-risk group KM curve illustrated at 521. The visualization of CFOD-TS difference between short term and long term survival patients is shown in FIG. 6, which illustrates relatively more highly aligned collagen fibers with the orientation co-occurrence frequency highlighted in diagonals of the matrix for a short term survival patient.

Figure 6:
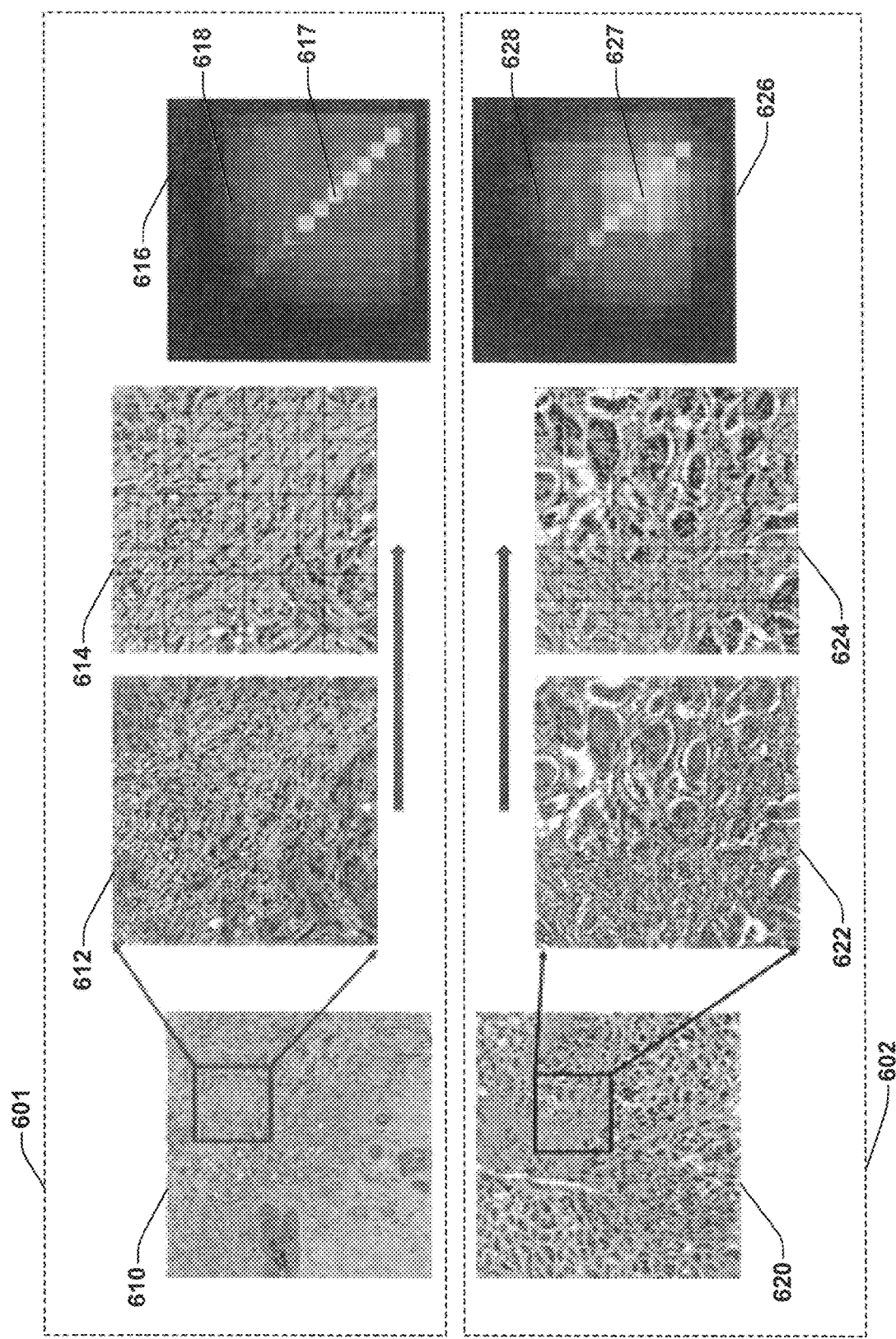
FIG. 6 illustrates tumor patches from regions of interest (ROI) pertaining to a short-term breast cancer survival case and a long-term breast cancer survival case according to various embodiments described herein.

FIG. 6 illustrates tumor patches from ROI pertaining to a short term survival case 601 and a long term survival case 602. Original tumor patches are illustrated at 610 for the short term survival case, and at 620 for the long-term survival case. Detected collagen fiber and epithelial masks are displayed in a local region of tumor patch for the short-term survival case at 612 and at 622 for the long-term survival case. Calculated collagen vectors are illustrated at 614 for the short-term survival case and at 624 for the long-term survival case. Collagen vector orientation co-occurrence matrices with warm color (617, 627) indicating a high frequency value and cold color (618, 628) indicating a low frequency are illustrated for the short term survival case at 616 and for the long term survival case at 626.

Embodiments described herein, including at least operations 100, 200, and 1000, and apparatus 700 or 800, resolve features extracted from digitized whole slide imagery at a higher order or higher level than a human can resolve in the human mind or with pencil and paper. For example, collagen orientation disorder features described herein that are not perceivable by the human eye may be detected by embodiments, and the prognoses or classifications generated by embodiments are not properties of a tissue that are perceivable by the human eye, computable using pencil and paper, or practically computed in the human mind. Embodiments thus perform actions, steps, processes, or other actions that are not practically performed in the human mind, at least because they require a processor or circuitry to access digitized images stored in a computer memory and to extract or compute features including the generation of orientation co-occurrence matrices and quantitative measurements of collagen fiber orientation disorder that are based on the digitized images and not on properties of tissue or the images that are perceivable by the human eye. Embodiments described herein use a combined order of specific rules, elements, operations, or components that render information into a specific format that is then used and applied to create desired results more accurately, more consistently, and with greater reliability than existing approaches, thereby producing the technical effect of improving the performance of the machine, computer, or system with which embodiments are implemented.

Embodiments automatically identify and determine the relative disorder in collage fiber orientation from standard of care digitized H&E stained WSIs of tissue demonstrating breast cancer. Compared to existing approaches, including deep learning recurrence prediction models, embodiments provide more accurate prognoses and more intuitive prognostic value.

Figure 7:
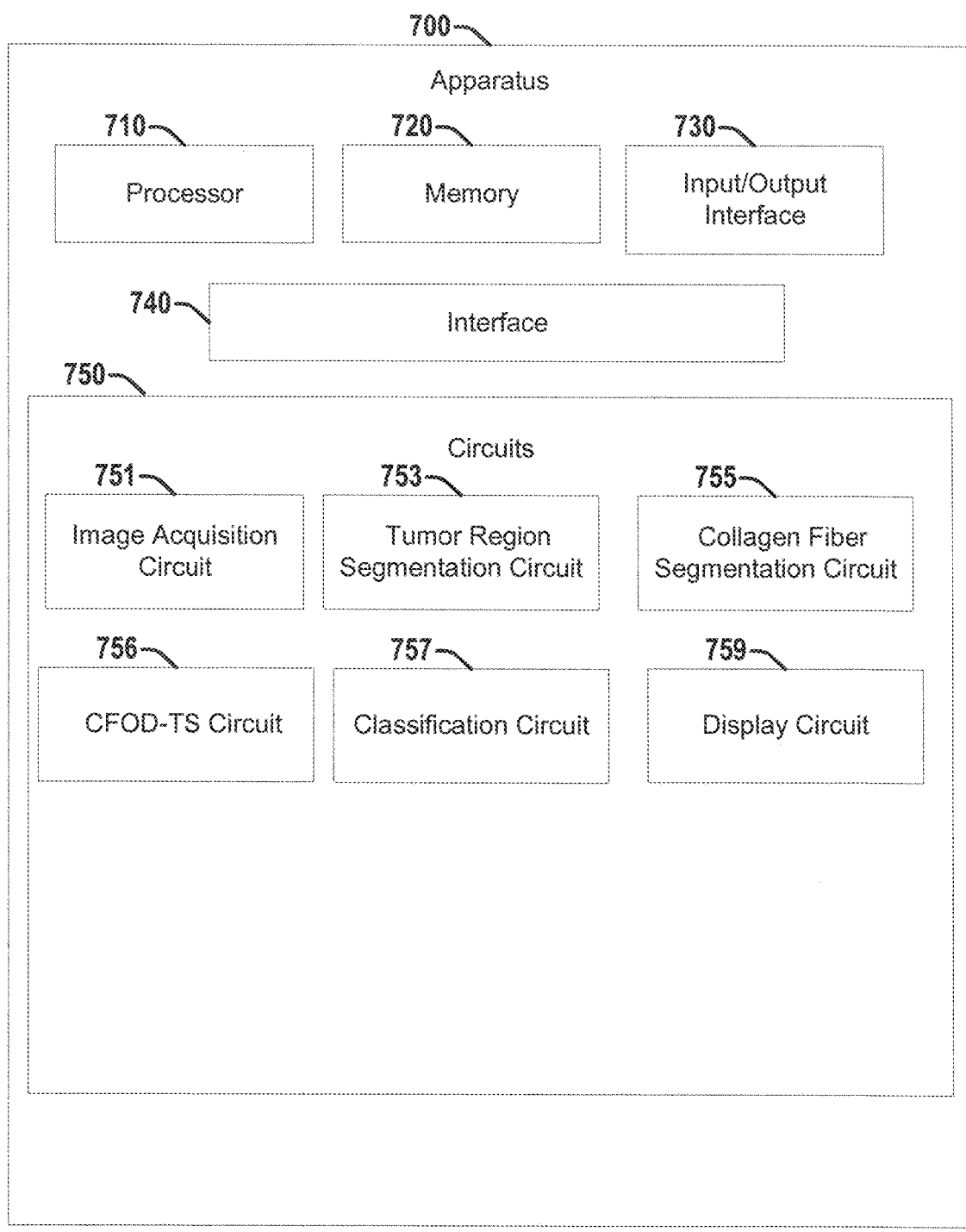
FIG. 7 illustrates an example apparatus configured to classify a patient based on a prognosis of disease free survival in breast cancer according to various embodiments described herein.

FIG. 7 illustrates an example apparatus 700. Apparatus 700 may be configured to generate a prognosis of disease free survival for a patient demonstrating ER+ breast cancer, and generate a classification of the patient into a positive class, for example high-risk of recurrence, or a negative class, for example, low-risk of recurrence, based on the prognosis. Apparatus 700 includes a processor 710. Apparatus 700 also includes a memory 720. Processor 710 may, in one embodiment, include circuitry such as, but not limited to, one or more single-core or multi-core processors. Processor 710 may include any combination of general-purpose processors and dedicated processors (e.g., graphics processors, application processors, etc.). The processors may be coupled with or may include memory (e.g. memory 720) or storage and may be configured to execute instructions stored in the memory 720 or storage to enable various apparatus, applications, or operating systems to perform the operations. Memory 720 is configured to store a digitized image of a region of interest (ROI) demonstrating breast cancer. The digitized image has a plurality of pixels, a pixel having an intensity. The digitized image is associated with a patient. Memory 720 may be further configured to store information associated with a patient associated with an image stored in memory 720, including clinical information associated with the patient.

Apparatus 700 also includes an input/output (I/O) interface 730, a set of circuits 750, and an interface 740 that connects the processor 710, the memory 720, the I/O interface 730, and the set of circuits 750. I/O interface 730 may be configured to transfer data between memory 720, processor 710, circuits 750, and external devices, for example, a breast cancer recurrence risk classification system, a CADx system, an MRI system, a CT system, or a digital whole slide scanner.

The set of circuits 750 includes image acquisition circuit 751. Image acquisition circuit 751 is configured to access a digitized image of a region of tissue demonstrating breast cancer. The digitized includes a plurality of pixels, a pixel having an intensity. In one embodiment, the digitized image is a digitized H&E stained WSI of a region of tissue demonstrating ER+ breast cancer scanned at 20× magnification. The digitized image includes a representation of a tumor region. In one embodiment, the digitized image includes a plurality of tumor patches. In one embodiment, a tumor patch has dimensions of 4000 pixels by 4000 pixels. In one embodiment, accessing the digitized image may include accessing a digitized image stored in a data storage device, including a hard disk drive, a solid state device, a tape drive, or accessing a digitized image over a local area network. Accessing the digitized image includes acquiring electronic data, reading from a computer file, receiving a computer file, reading from a computer memory, or other computerized activity not practically performed in a human mind.

The set of circuits 750 also includes tumor region segmentation circuit 753. Tumor region segmentation circuit 753 is configured to segment a tumor region represented in the digitized image. In one embodiment, tumor region segmentation circuit 753 is configured to segment the tumor region using a convolutional neural network deep learning model segmentation technique. Tumor region segmentation circuit 753 is further configured to define at least one tumor patch. A tumor patch may be a square patch having dimensions of 4000 pixels in the x-axis by 4000 pixels in the y-axis. In another embodiment, a tumor patch may have other, different dimensions, for example, 2000 pixels in the x-axis by 2000 pixels in the y-axis.

The set of circuits 750 also includes collagen fiber segmentation circuit 755. Collagen fiber segmentation circuit 755 is configured to segment collagen fibers represented in the tumor region according to various techniques described herein. Collagen fiber segmentation circuit 755 is also configured to compute a plurality of collagen vectors based on the segmented collagen fibers. Collagen fiber segmentation circuit 755 is further configured to generate an orientation co-occurrence matrix based on the plurality of collagen vectors. In one embodiment, collagen fiber segmentation circuit 755 is configured to segment collagen fibers represented in the digitized image using a basic image feature (BIF) segmentation approach. In one embodiment, collagen fiber segmentation circuit 755 is configured to generate the orientation co-occurrence matrix based on the plurality of collagen vectors by calculating the frequency with which a first collagen vector with a first orientation x co-occurs with a second, different collagen vector with a second orientation y weighted by a corresponding vector length. In one embodiment, collagen fiber segmentation circuit 755 is configured to generate the orientation co-occurrence matrix by normalizing the co-occurrence matrix by computing the total summed matrix element values, and dividing the co-occurrence matrix by the total summed matrix element values.

The set of circuits 750 also includes collagen fiber orientation disorder feature (CFOD-TS) circuit 756. CFOD-TS circuit 756 is configured to compute a set of collagen fiber orientation disorder features from tumor-associated stroma based on the orientation co-occurrence matrix. In embodiment, the set of collagen fiber orientation disorder features includes an orientation difference entropy feature. In another embodiment, the set of collagen fiber orientation disorder features includes at least one of an orientation difference entropy feature, an entropy feature, or an orientation difference variance feature.

The set of circuits 750 also includes classification circuit 757. Classification circuit 757 is configured to determine a value of a member of the set of collagen fiber orientation features. Classification circuit 757 is also configured to, upon determining that a member of the set of collagen fiber orientation features exceeds a threshold value, generate a prognosis of the region of tissue as unlikely to experience breast cancer recurrence. Classification circuit 757 is also configured to, upon determining that the member of the set of collagen fiber orientation features is less than or equal to the threshold value, generate a prognosis of the region of tissue as likely to experience breast cancer recurrence. In one embodiment, the threshold value is 2.25. In another embodiment, another, different threshold value or values may be employed. Classification circuit 757 is further configured to generate a classification of the patient as high-risk of recurrence or low-risk of recurrence based, at least in part, on the prognosis. For example, a patient associated with a prognosis of unlikely to experience breast cancer recurrence may be classified as low-risk of recurrence, while a different patient associated with a prognosis of likely to experience breast cancer recurrence may be classified as high-risk of recurrence. Other classification schemes may be employed.

The set of circuits 750 also includes a display circuit 759. Display circuit 759 is configured to display the classification according to various embodiments described herein. For example, display circuit 759 may be configured to display the classification on a computer monitor, a smartphone display, a tablet display, or other displays, or to print the classification. Display circuit 759 may be configured to optionally display the prognosis, a member of the set of collagen fiber orientation features, a value associated with the member of the set of collagen fiber orientation features, the orientation co-occurrence matrix, a member of the plurality of collagen vectors, or the digitized image.

Figure 8:
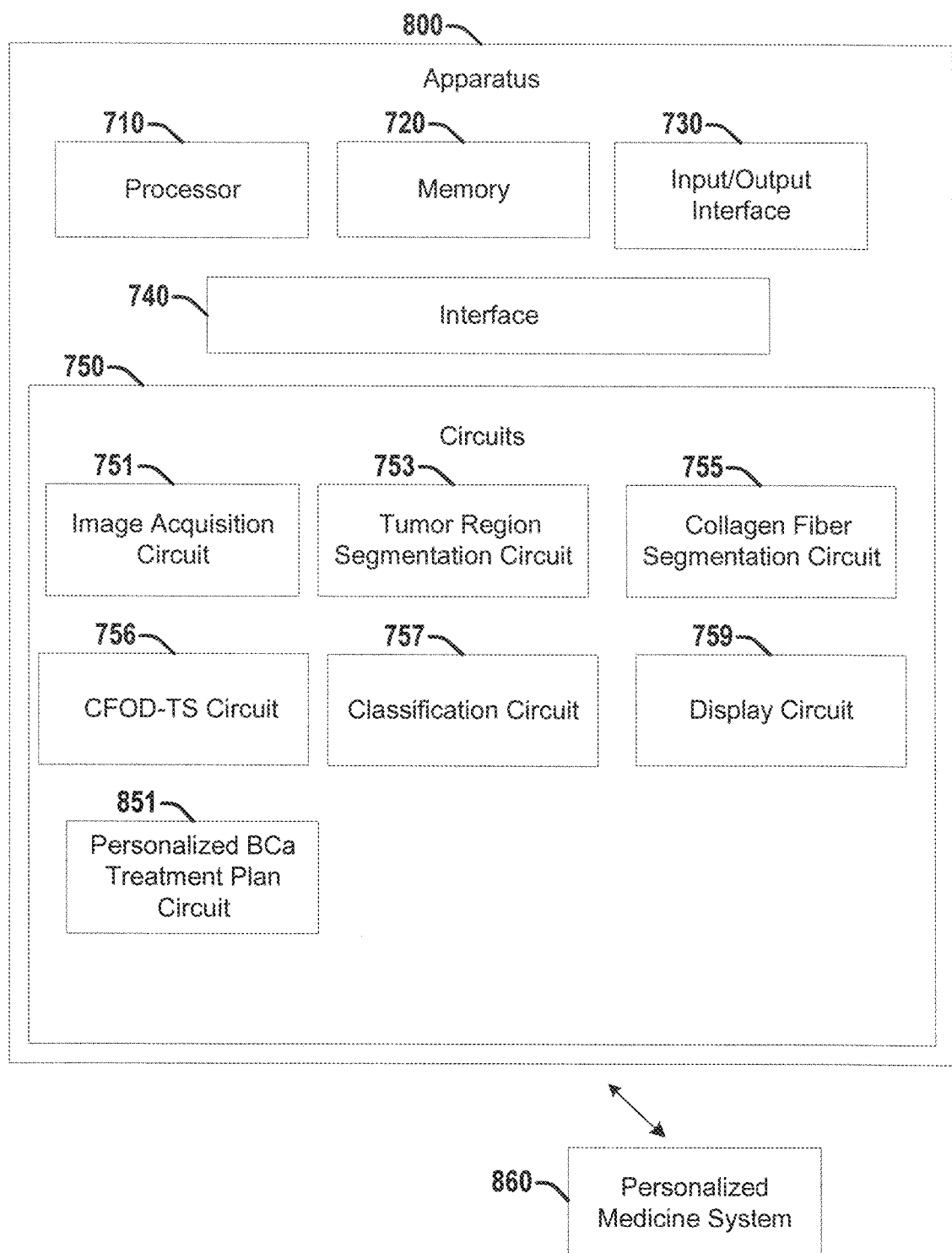
FIG. 8 illustrates an example apparatus configured to classify a patient based on a prognosis of disease free survival in breast cancer according to various embodiments described herein.

FIG. 8 illustrates an apparatus 800 that is similar to apparatus 700 but that includes additional elements and details. Apparatus 800 includes a personalized breast cancer (BCa) treatment plan circuit 851. Personalized BCa treatment plan circuit 851 is configured to generate a personalized BCa treatment plan based, at least in part, on the classification. Personalized BCa treatment plan circuit 851 may be configured to generate the personalized BCa treatment plan based, at least in part, on the classification, and further based on at least one of the prognosis or the digitized image. Personalized BCa treatment plan circuit 851 is also configured to optionally control display circuit 759 to display the personalized BCa treatment plan. In one embodiment, personalized BCa treatment plan circuit 851 may be configured to compute a first dosage or dosage schedule of a first therapeutic agent based, at least in part, on the classification when the patient is classified as high-risk of recurrence, or a second, different dosage or dosage schedule of a therapeutic agent based, at least in part, on the classification when the patient is classified as low-risk of recurrence. A therapeutic agent may include, for example, an adjuvant chemotherapy agent, an immunotherapy agent, or other type of therapeutic agent. Personalized BCa treatment plan circuit 851 may also be configured to generate different follow-up or monitoring schedules depending on the classification. For example, personalized BCa treatment plan circuit 851 may to generate a first follow-up or monitoring schedule for a patient classified as low-risk of recurrence, or may generate a second, different follow-up or monitoring schedule for a patient classified as high-risk of recurrence.

Apparatus 800 may include, or be operably connected to, a personalized medicine system 860. Apparatus 800 may be configured to transmit the classification, personalized BC treatment plan, or other information to personalized medicine system 860. Apparatus 800 may be configured to control personalized medicine system 860 to display at least one of the classification, the personalized BCa treatment plan, the digitized image, prognosis, or other information. In one embodiment, personalized medicine system 860 may be configured as a member of circuits 750.

Figure 9:
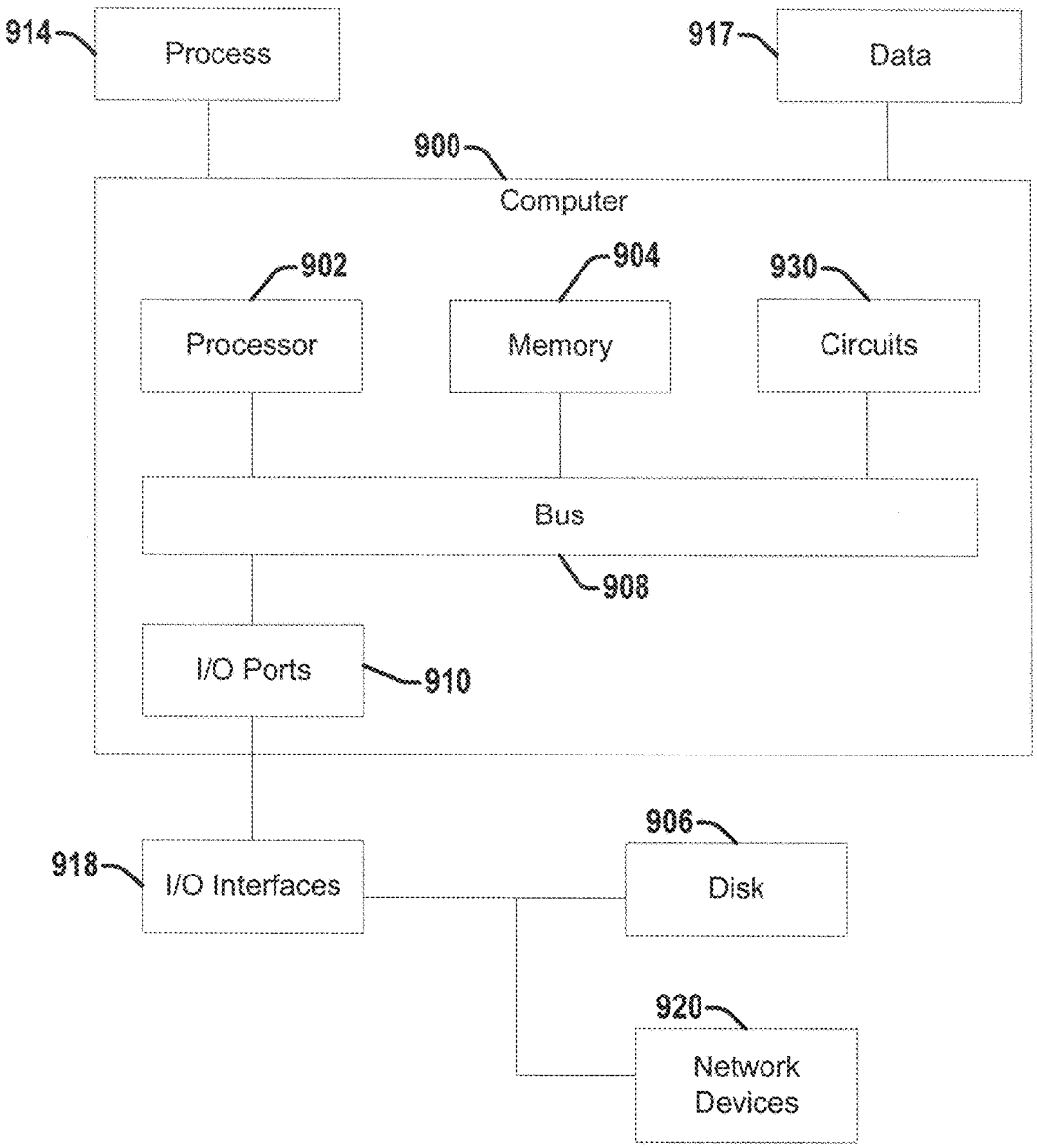
FIG. 9 illustrates an example computer in which embodiments described herein may operate.

FIG. 9 illustrates an example computer 900 in which example methods illustrated herein can operate and in which example methods, apparatus, circuits, operations, or logics may be implemented. In different examples, computer 900 may be part of a breast cancer prognosis system or apparatus, a CADx system, an MRI system, a CT system, a digital whole slide scanner, or a personalized medicine system, or may be operably connectable to a breast cancer prognosis system or apparatus, a CADx system, an MRI system, a CT system, a digital whole slide scanner, or a personalized medicine system.

Computer 900 includes a processor 902, a memory 904, and input/output (I/O) ports 910 operably connected by a bus 908. In one example, computer 900 may include a set of logics or circuits 930 that perform operations for or a method of generating a classification of a breast cancer patient as high-risk of recurrence or low-risk of recurrence based, at least in part, on a prognosis based on a CFOD-TS feature or features extracted from a digitized WSI associated with the patient. Thus, the set of circuits 930, whether implemented in computer 900 as hardware, firmware, software, and/or a combination thereof may provide means (e.g., hardware, firmware, circuits) for distinguishing breast cancer patients based on a CFOD-TS feature or features extracted from a digitized WSI associated with the patient, or classifying a breast cancer patient as high-risk of recurrence or low-risk of recurrence on digitized WSI imagery. In different examples, the set of circuits 930 may be permanently and/or removably attached to computer 900.

Processor 902 can be a variety of various processors including dual microprocessor and other multi-processor architectures. Processor 902 may be configured to perform steps of methods claimed and described herein. Memory 904 can include volatile memory and/or non-volatile memory. A disk 906 may be operably connected to computer 900 via, for example, an input/output interface (e.g., card, device) 918 and an input/output port 910. Disk 906 may include, but is not limited to, devices like a magnetic disk drive, a tape drive, a Zip drive, a flash memory card, or a memory stick. Furthermore, disk 906 may include optical drives like a CD-ROM or a digital video ROM drive (DVD ROM). Memory 904 can store processes 914 or data 917, for example. Data 917 may, in one embodiment, include digitized images, including digitized H&E stained WSI images of tissue demonstrating breast cancer. Disk 906 or memory 904 can store an operating system that controls and allocates resources of computer 900.

Bus 908 can be a single internal bus interconnect architecture or other bus or mesh architectures. While a single bus is illustrated, it is to be appreciated that computer 900 may communicate with various devices, circuits, logics, and peripherals using other buses that are not illustrated (e.g., PCIE, SATA, Infiniband, 1394, USB, Ethernet).

Computer 900 may interact with input/output devices via I/O interfaces 918 and input/output ports 910. Input/output devices can include, but are not limited to, digital whole slide scanners, CT systems, MRI systems, an optical microscope, a keyboard, a microphone, a pointing and selection device, cameras, video cards, displays, disk 906, network devices 920, or other devices. Input/output ports 910 can include but are not limited to, serial ports, parallel ports, or USB ports.

Computer 900 may operate in a network environment and thus may be connected to network devices 920 via I/O interfaces 918 or I/O ports 910. Through the network devices 920, computer 900 may interact with a network. Through the network, computer 900 may be logically connected to remote computers. The networks with which computer 900 may interact include, but are not limited to, a local area network (LAN), a wide area network (WAN), or other networks, including the cloud.

FIG. 10 illustrates a flow diagram of an example method or set of operations 1000 for classifying a breast cancer patient as high-risk of recurrence or low-risk of recurrence based on collagen fiber orientation disorder from tumor-associated stroma. Operations 1000 includes acquiring electronic data, reading from a computer file, receiving a computer file, reading from a computer memory, or other computerized activity not practically performed in a human mind.

Operations 1000 includes, at 1010 accessing a digitized hematoxylin and eosin (H&E) stained whole slide image (WSI) of a region of tissue demonstrating ER+ breast cancer. In one embodiment, the digitized H&E stained WSI is scanned at 20× magnification. The digitized H&E stained WSI is associated with a patient. Accessing the digitized H&E stained WSI may, in one embodiment, also include accessing clinical data associated with a patient.

Operations 1000 also includes, at 1020 segmenting a tumor region represented in the digitized image. In one embodiment, segmenting the tumor region may include segmenting the tumor region using a deep learning model, for example, a convolutional neural network trained to segment a tumor region represented in digitized WSI imagery. In another embodiment, segmenting the tumor region may include annotating or segmenting the tumor region using Automated Slide Analysis Platform (ASAP), or ImageScope, or other annotation or segmentation technique. In another embodiment, a segmented tumor region may be pre-defined in the accessed digitized H&E stained WSI.

Operations 1000 also includes, at 1022, defining a plurality of tumor patches based on the segmented tumor region. In one embodiment, a member of the plurality of tumor patches has dimensions of 4000 pixels in the x-axis by 4000 pixels in the y-axis. In another embodiment, a tumor patch may have other, different dimensions, for example, 2000 pixels by 2000 pixels.

Operations 1000 also includes, at 1030, segmenting collagen fibers represented in the plurality of tumor patches. In one embodiment, segmenting collagen fibers represented in the plurality of tumor patches may include using basic image feature (BIF) segmentation according to various embodiments described herein.

Operations 1000 also includes, at 1040, computing a plurality of collagen vectors. The plurality of collagen vectors is computed based on the segmented collagen fibers according to various embodiments described herein.

Operations 1000 also includes, at 1050, generating a collagen vector orientation co-occurrence matrix based on the plurality of collagen vectors according to various embodiments described herein. In one embodiment, generating the collagen vector orientation co-occurrence matrix based on the plurality of collagen vectors comprises calculating the frequency with which a first collagen vector having a first orientation x co-occurs with a second, different collagen vector having a second orientation y weighted by a corresponding vector length.

Operations 1000 also includes, at 1060, computing an orientation difference entropy feature based on the collagen vector orientation co-occurrence matrix. The orientation difference entropy feature has a value. For example, in one embodiment, the orientation different entropy feature may have a value of 0 to 2.89. In another embodiment, the orientation different entropy feature may have a different value.

Operations 1000 also includes, at 1070, determining the value of the orientation difference entropy feature. Determining the value of the orientation difference entropy feature may include acquiring electronic data, reading from a computer file, receiving a computer file, reading from a computer memory, or other computerized activity not practically performed in a human mind.

Operations 1000 also includes, at 1072, upon determining that the value of the orientation difference entropy feature exceeds a threshold value, generating a prognosis of the patient as unlikely to experience breast cancer recurrence. In one embodiment, the threshold value is 2.25. In another embodiment, the threshold value may be another, different value.

Operations 1000 also includes, at 1074, upon determining that the value of the orientation difference entropy feature is less than or equal to the threshold value, generating a prognosis of the patient as likely to experience breast cancer recurrence.

Operations 1000 also includes, at 1080, generating a classification of the patient as high-risk of recurrence or low-risk of recurrence based, at least in part, on the prognosis. In one embodiment, the classification may be generated based on the prognosis. In another embodiment, the classification may be generated based on the prognosis and optionally on at least one of the digitized image, a value of the orientation difference entropy feature, or on clinical data associated with the patient. The classification may be generated according to various embodiments described herein.

Operations 1000 further includes, at 1090, displaying the classification according to various techniques described herein. Displaying the classification may, in one embodiment, further include optionally displaying the digitized H&E stained WSI, the prognosis, clinical data associated with the patient, or other data.

In one embodiment, operations 1000 also includes, at 1092, generating a personalized breast cancer treatment plan based on the classification, according to various techniques described herein. In another embodiment, the personalized breast cancer treatment plan may be generated based, at least in part, on the classification and at least one of the digitized H&E stained WSI, the prognosis, clinical data associated with the patient, or other data. In this embodiment, operations 1000 further includes, at 1094, displaying the personalized breast cancer treatment plan according to various techniques described herein.

Example 1 comprises a non-transitory computer-readable storage device storing computer-executable instructions that, in response to execution, cause a processor to perform operations, the operations comprising: accessing a digitized image of a region of tissue demonstrating breast cancer pathology, where the digitized image includes a plurality of pixels, a pixel having an intensity, where the digitized image is associated with a patient; segmenting a tumor region represented in the digitized image; segmenting collagen fibers represented in the tumor region; computing a plurality of collagen vectors based on the segmented collagen fibers; generating an orientation co-occurrence matrix based on the plurality of collagen vectors; computing a set of collagen fiber orientation disorder features based on the orientation co-occurrence matrix; upon determining that a member of the set of collagen fiber orientation disorder features exceeds a threshold value: generating a prognosis of the region of tissue as unlikely to experience breast cancer recurrence; upon determining that the member of the set of collagen fiber orientation disorder features is less than or equal to the threshold value: generating a prognosis of the region of tissue as likely to experience breast cancer recurrence; generating a classification of the patient as high-risk of recurrence or low-risk of recurrence based, at least in part, on the prognosis; and displaying the classification.

Example 2 comprises the subject matter of any variation of any of example(s) 1, where the digitized image is a digitized hematoxylin and eosin (H&E) stained whole slide image (WSI) of a region of tissue demonstrating ER+ breast cancer.

Example 3 comprises the subject matter of any variations of any of example(s) 1-2, where the digitized image is scanned at 20× magnification, and where the tumor region comprises a plurality of tumor patches, where a tumor patch has dimensions of 4000 pixels by 4000 pixels.

Example 4 comprises the subject matter of any variations of any of example(s) 1-3, where segmenting collagen fibers represented in the digitized image comprises segmenting collagen fibers represented in the digitized image using a basic image feature (BIF) segmentation approach.

Example 5 comprises the subject matter of any variations of any of example(s) 1-4, where generating the orientation co-occurrence matrix based on the plurality of collagen vectors comprises calculating the frequency with which a first collagen vector with a first orientation x co-occurs with a second, different collagen vector with a second orientation y weighted by a corresponding vector length.

Example 6 comprises the subject matter of any variations of any of example(s) 1-5, where generating the orientation co-occurrence matrix further comprises normalizing the co-occurrence matrix by computing the total summed matrix element values, and dividing the co-occurrence matrix by the total summed matrix element values.

Example 7 comprises the subject matter of any variations of any of example(s) 1-6, where the set of collagen fiber orientation disorder features includes an orientation difference entropy feature.

Example 8 comprises the subject matter of any variations of any of example(s) 1-7, where the threshold value is 2.25.

Example 9 comprises the subject matter of any variations of any of example(s) 1-8, where the set of collagen fiber orientation disorder features includes at least one of an orientation difference entropy feature, an entropy feature, or an orientation difference variance feature.

Example 10 comprises the subject matter of any variations of any of example(s) 1-9, the operations further comprising generating a personalized breast cancer treatment plan based, at least in part, on the classification.

Example 11 comprises the subject matter of any variations of any of example(s) 1-10, the operations further comprising displaying the personalized breast cancer treatment plan.

Example 12 comprises an apparatus comprising: a processor; a memory configured to store a digitized image of a region of interest (ROI) demonstrating breast cancer, the digitized image having a plurality of pixels, a pixel having an intensity, where the digitized image is associated with a patient; an input/output (I/O) interface; a set of circuits; and an interface that connects the processor, the memory, the I/O interface, and the set of circuits, the set of circuits comprising: an image acquisition circuit configured to: access a digitized image of a region of tissue demonstrating breast cancer pathology, where the digitized image includes a plurality of pixels, a pixel having an intensity, where the digitized image is associated with a patient; a tumor region segmentation circuit configured to: segment a tumor region represented in the digitized image; a collagen fiber segmentation circuit configured to: segment collagen fibers represented in the tumor region; compute a plurality of collagen vectors based on the segmented collagen fibers; and generate an orientation co-occurrence matrix based on the plurality of collagen vectors; a collagen fiber orientation disorder feature (CFOD-TS) circuit configured to: compute a set of collagen fiber orientation disorder features based on the orientation co-occurrence matrix; a classification circuit configured to: determine a value of a member of the set of collagen fiber orientation disorder features; upon determining that a member of the set of collagen fiber orientation disorder features exceeds a threshold value: generate a prognosis of the region of tissue as unlikely to experience breast cancer recurrence; upon determining that the member of the set of collagen fiber orientation disorder features is less than or equal to the threshold value: generate a prognosis of the region of tissue as likely to experience breast cancer recurrence; and generate a classification of the patient as high-risk of recurrence or low-risk of recurrence based, at least in part, on the prognosis; and a display circuit configured to display the classification.

Example 13 comprises the subject matter of any variation of any of example(s) 12, where the digitized image is a digitized hematoxylin and eosin (H&E) stained whole slide image (WSI) of a region of tissue demonstrating ER+ breast cancer scanned at 20× magnification, where the tumor region comprises a plurality of tumor patches, where a tumor patch has dimensions of 4000 pixels by 4000 pixels.

Example 14 comprises the subject matter of any variation of any of example(s) 12-13, where the collagen fiber segmentation circuit is configured to segment collagen fibers represented in the digitized image using a basic image feature (BIF) segmentation approach.

Example 15 comprises the subject matter of any variation of any of example(s) 12-14, where the collagen fiber segmentation circuit is configured to generate the orientation co-occurrence matrix based on the plurality of collagen vectors by calculating the frequency with which a first collagen vector with a first orientation x co-occurs with a second, different collagen vector with a second orientation y weighted by a corresponding vector length.

Example 16 comprises the subject matter of any variation of any of example(s) 12-15, the collagen fiber segmentation circuit is configured to generate the orientation co-occurrence matrix by normalizing the co-occurrence matrix by computing the total summed matrix element values, and dividing the co-occurrence matrix by the total summed matrix element values.

Example 17 comprises the subject matter of any variation of any of example(s) 12-16, where the set of collagen fiber orientation disorder features includes at least one of an orientation difference entropy feature, an entropy feature, or an orientation difference variance feature.

Example 18 comprises the subject matter of any variation of any of example(s) 12-17, where the threshold value is 2.25.

Example 19 comprises the subject matter of any variation of any of example(s) 12-18, the set of circuits further comprising a personalized breast cancer treatment plan circuit configured to: generate a personalized breast cancer treatment plan based, at least in part, on the classification; and control the display circuit to display the personalized breast cancer treatment plan.

Example 20 comprises a non-transitory computer-readable storage device storing computer-executable instructions that, in response to execution, cause a processor to perform operations comprising: accessing a digitized hematoxylin and eosin (H&E) stained whole slide image (WSI) of a region of tissue demonstrating ER+ breast cancer scanned at 20× magnification, where the region of tissue includes a tumor region, where the digitized H&E stained WSI image is associated with a patient; generating a segmented tumor region by segmenting the tumor region represented in the digitized H&E stained WSI image; defining a plurality of tumor patches based on the segmented tumor region, where a tumor patch has dimensions of 4000 pixels by 4000 pixels; segmenting collagen fibers represented in the plurality of tumor patches using basic image feature (BIF) segmentation; computing a plurality of collagen vectors based on the segmented collagen fibers; generating a collagen vector orientation co-occurrence matrix based on the plurality of collagen vectors; computing an orientation difference entropy feature based on the collagen vector orientation co-occurrence matrix, the orientation difference entropy feature having a value; upon determining that the value of the orientation difference entropy feature exceeds a threshold value: generating a prognosis of the patient as unlikely to experience breast cancer recurrence; upon determining that the value of the orientation difference entropy feature is less than or equal to the threshold value: generating a prognosis of the patient as likely to experience breast cancer recurrence; generating a classification of the patient as high-risk of recurrence or low-risk of recurrence based, at least in part, on the prognosis; and displaying the classification.

Example 21 comprises a machine readable storage device that stores instructions for execution by a processor to perform any of the described operations of examples 1-20.

Example 22 comprises an apparatus comprising: a memory; and one or more processors configured to: perform any of the described operations of examples 1-20.

Examples herein can include subject matter such as an apparatus, a breast cancer recurrence risk classification system or apparatus, a personalized medicine system, a CADx system, a whole slide scanner, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or operations or of an apparatus or system classifying a breast cancer patients with high-risk of recurrence or low-risk of recurrence based on CFOD-TS features extracted from medical imagery of the breast cancer patient, for example, a digitized H&E stained WSI associated with the patient, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that, in response to execution, cause a processor to perform operations, the operations comprising:
   accessing a digitized image of a region of tissue demonstrating breast cancer pathology, where the digitized image includes a plurality of pixels, a pixel having an intensity, where the digitized image is associated with a patient;
   segmenting a tumor region represented in the digitized image;
   segmenting collagen fibers represented in the tumor region;
   computing a plurality of collagen vectors based on the segmented collagen fibers;
   generating an orientation co-occurrence matrix based on the plurality of collagen vectors;
   computing a set of collagen fiber orientation disorder features based on the orientation co-occurrence matrix;
   upon determining that a member of the set of collagen fiber orientation disorder features exceeds a threshold value:
      generating a prognosis of the region of tissue as unlikely to experience breast cancer recurrence;
   upon determining that the member of the set of collagen fiber orientation disorder features is less than or equal to the threshold value:
      generating a prognosis of the region of tissue as likely to experience breast cancer recurrence;
   generating a classification of the patient as high-risk of recurrence or low-risk of recurrence based, at least in part, on the prognosis; and
   displaying the classification.

2. The non-transitory computer-readable storage device of claim 1 where the digitized image is a digitized hematoxylin and eosin (H&E) stained whole slide image (WSI) of a region of tissue demonstrating ER+ breast cancer.

3. The non-transitory computer-readable storage device of claim 2, where the digitized image is scanned at 20× magnification, and where the tumor region comprises a plurality of tumor patches, where a tumor patch has dimensions of 4000 pixels by 4000 pixels.

4. The non-transitory computer-readable storage device of claim 1, where segmenting collagen fibers represented in the digitized image comprises segmenting collagen fibers represented in the digitized image using a basic image feature (BIF) segmentation approach.

5. The non-transitory computer-readable storage device of claim 1, where generating the orientation co-occurrence matrix based on the plurality of collagen vectors comprises calculating the frequency with which a first collagen vector with a first orientation x co-occurs with a second, different collagen vector with a second orientation y weighted by a corresponding vector length.

6. The non-transitory computer-readable storage device of claim 4, where generating the orientation co-occurrence matrix further comprises normalizing the co-occurrence matrix by computing the total summed matrix element values, and dividing the co-occurrence matrix by the total summed matrix element values.

7. The non-transitory computer-readable storage device of claim 1 where the set of collagen fiber orientation disorder features includes an orientation difference entropy feature.

8. The non-transitory computer-readable storage device of claim 7, where the threshold value is 2.25.

9. The non-transitory computer-readable storage device of claim 1, where the set of collagen fiber orientation disorder features includes at least one of an orientation difference entropy feature, an entropy feature, or an orientation difference variance feature.

10. The non-transitory computer-readable storage device of claim 1, the operations further comprising generating a personalized breast cancer treatment plan based, at least in part, on the classification.

11. The non-transitory computer-readable storage device of claim 10, the operations further comprising displaying the personalized breast cancer treatment plan.

12. An apparatus comprising:
   a processor;
   a memory configured to store a digitized image of a region of interest (ROI) demonstrating breast cancer, the digitized image having a plurality of pixels, a pixel having an intensity, where the digitized image is associated with a patient;
   an input/output (I/O) interface;
   a set of circuits; and
   an interface that connects the processor, the memory, the I/O interface, and the set of circuits, the set of circuits comprising:
      an image acquisition circuit configured to:
         access a digitized image of a region of tissue demonstrating breast cancer pathology, where the digitized image includes a plurality of pixels, a pixel having an intensity, where the digitized image is associated with a patient;
      a tumor region segmentation circuit configured to:
         segment a tumor region represented in the digitized image;
      a collagen fiber segmentation circuit configured to:
         segment collagen fibers represented in the tumor region;
         compute a plurality of collagen vectors based on the segmented collagen fibers; and
         generate an orientation co-occurrence matrix based on the plurality of collagen vectors;
      a collagen fiber orientation disorder feature (CFOD-TS) circuit configured to:
         compute a set of collagen fiber orientation disorder features based on the orientation co-occurrence matrix;
      a classification circuit configured to:
         determine a value of a member of the set of collagen fiber orientation disorder features;
         upon determining that a member of the set of collagen fiber orientation disorder features exceeds a threshold value:
            generate a prognosis of the region of tissue as unlikely to experience breast cancer recurrence;

upon determining that the member of the set of collagen fiber orientation disorder features is less than or equal to the threshold value:
generate a prognosis of the region of tissue as likely to experience breast cancer recurrence; and
generate a classification of the patient as high-risk of recurrence or low-risk of recurrence based, at least in part, on the prognosis; and
a display circuit configured to display the classification.

13. The apparatus of claim 12, where the digitized image is a digitized hematoxylin and eosin (H&E) stained whole slide image (WSI) of a region of tissue demonstrating ER+ breast cancer scanned at 20× magnification, where the tumor region comprises a plurality of tumor patches, where a tumor patch has dimensions of 4000 pixels by 4000 pixels.

14. The apparatus of claim 12, where the collagen fiber segmentation circuit is configured to segment collagen fibers represented in the digitized image using a basic image feature (BIF) segmentation approach.

15. The apparatus of claim 12, where the collagen fiber segmentation circuit is configured to generate the orientation co-occurrence matrix based on the plurality of collagen vectors by calculating the frequency with which a first collagen vector with a first orientation x co-occurs with a second, different collagen vector with a second orientation y weighted by a corresponding vector length.

16. The apparatus of claim 12, where the collagen fiber segmentation circuit is configured to generate the orientation co-occurrence matrix by normalizing the co-occurrence matrix by computing the total summed matrix element values, and dividing the co-occurrence matrix by the total summed matrix element values.

17. The apparatus of claim 12, where the set of collagen fiber orientation disorder features includes at least one of an orientation difference entropy feature, an entropy feature, or an orientation difference variance feature.

18. The apparatus of claim 17, where the threshold value is 2.25.

19. The apparatus of claim 12, the set of circuits further comprising a personalized breast cancer treatment plan circuit configured to:
generate a personalized breast cancer treatment plan based, at least in part, on the classification; and
control the display circuit to display the personalized breast cancer treatment plan.

20. A non-transitory computer-readable storage device storing computer-executable instructions that, in response to execution, cause a processor to perform operations comprising:
accessing a digitized hematoxylin and eosin (H&E) stained whole slide image (WSI) of a region of tissue demonstrating ER+ breast cancer scanned at 20× magnification, where the region of tissue includes a tumor region, where the digitized H&E stained WSI image is associated with a patient;
generating a segmented tumor region by segmenting the tumor region represented in the digitized H&E stained WSI image;
defining a plurality of tumor patches based on the segmented tumor region, where a tumor patch has dimensions of 4000 pixels by 4000 pixels;
segmenting collagen fibers represented in the plurality of tumor patches using basic image feature (BIF) segmentation;
computing a plurality of collagen vectors based on the segmented collagen fibers;
generating a collagen vector orientation co-occurrence matrix based on the plurality of collagen vectors;
computing an orientation difference entropy feature based on the collagen vector orientation co-occurrence matrix, the orientation difference entropy feature having a value;
upon determining that the value of the orientation difference entropy feature exceeds a threshold value:
generating a prognosis of the patient as unlikely to experience breast cancer recurrence;
upon determining that the value of the orientation difference entropy feature is less than or equal to the threshold value:
generating a prognosis of the patient as likely to experience breast cancer recurrence;
generating a classification of the patient as high-risk of recurrence or low-risk of recurrence based, at least in part, on the prognosis; and
displaying the classification.

* * * * *